US005739404A

United States Patent [19]
Darsow et al.

[11] Patent Number: 5,739,404
[45] Date of Patent: Apr. 14, 1998

[54] PROCESS FOR PREPARING A MIXTURE OF AMINO-METHYL-CYCLOHEXANES AND DIAMINO-METHYL-CYCLOHEXANES

[75] Inventors: Gerhard Darsow, Krefeld; Gerd-Michael Petruck, Erkrath, both of Germany

[73] Assignee: Bayer Aktiengesellschaft, Leverkusen, Germany

[21] Appl. No.: 822,253

[22] Filed: Mar. 20, 1997

[30] Foreign Application Priority Data

Apr. 3, 1996 [DE] Germany .................. 196 13 332.7

[51] Int. Cl.⁶ ............................................ C07C 209/72
[52] U.S. Cl. ...................................... 564/450; 564/451
[58] Field of Search ................................ 564/450, 451

[56] References Cited

U.S. PATENT DOCUMENTS

| | | | |
|---|---|---|---|
| 3,424,792 | 1/1969 | Cross | 564/461 |
| 3,445,516 | 5/1969 | Cross | 564/451 |
| 3,520,928 | 7/1970 | Greco | 564/450 |
| 3,657,152 | 4/1972 | Cenker et al. | 502/174 |
| 4,057,513 | 11/1977 | Biedermann et al. | 252/459 |
| 4,161,492 | 7/1979 | Weissel | 564/305 |
| 4,186,145 | 1/1980 | Weissel | 564/451 |
| 5,322,965 | 6/1994 | Immel et al. | 564/446 |

FOREIGN PATENT DOCUMENTS

| | | |
|---|---|---|
| 0091028 | 10/1983 | European Pat. Off. . |
| 0501265 | 9/1992 | European Pat. Off. . |
| 1618638 | 2/1971 | Germany . |
| 2024858 | 7/1971 | Germany . |
| 2132547 | 1/1973 | Germany . |
| 2502893 | 7/1976 | Germany . |
| 2506348 | 9/1976 | Germany . |
| 2745172 | 4/1979 | Germany . |

*Primary Examiner*—Richard L. Raymond
*Attorney, Agent, or Firm*—Sprung Kramer Schaefer & Briscoe

[57] ABSTRACT

For the continuous preparation of a mixture of amino-methyl-cyclohexanes and diamino-methyl-cyclohexanes by catalytic hydrogenation of diamino-toluenes with hydrogen at temperatures of from 150° to 260° C. and an $H_2$ pressure of from 20 to 500 bar, use is made of reduced support-free catalysts which are produced from pressed powders of cobalt, manganese, copper and alkaline earth metal (hydr) oxides, with or without a content of at least one (hydr)oxide of metals of transition group V and/or VI of the Periodic Table of the Elements (Mendeleev).

14 Claims, No Drawings

PROCESS FOR PREPARING A MIXTURE OF AMINO-METHYL-CYCLOHEXANES AND DIAMINO-METHYL-CYCLOHEXANES

BACKGROUND OF THE INVENTION

1. Field of the Invention

The invention relates to a continuous process for preparing a mixture of amino-methyl-cyclohexanes and diamino-methyl-cyclohexanes in variable amounts by catalytic pressure hydrogenation of diamino-toluenes with hydrogen at elevated temperature using catalysts prepared by reduction of shaped bodies comprising pressed powders of cobalt, manganese, copper and alkaline earth metal (hydr)oxides, where the shaped bodies can have a content of one or more (hydr)oxides of metals of transition group V and/or VI of the Periodic Table of the Elements (Mendeleev).

Amino-methyl-cyclohexanes are used for preparing aging inhibitors for rubbers and plastics, as corrosion inhibitors and as precursors for textile auxiliaries and crop protection agents.

Diamino-methyl-cyclohexanes are used for producing powder coating hardeners, epoxide hardeners, lightfast surface coating resins and aqueous surface coating resin dispersions.

2. Description of the Related Art

It is known that diamino-methyl-cyclohexanes can be prepared by pressure hydrogenation of diamino-toluenes. In this hydrogenation, catalysts used are nickel alloys with molybdenum, ruthenium, tantalum, titanium (EP 091 028) or cobalt oxide (DE 16 18 638/DE 2 024 858/JP 48/32 845 (1973)), wherein the experimental examples describe exclusively batchwise processes and the reaction products specified are exclusively diamino-methyl-cyclohexanes.

Other batch processes mainly use costly noble metals on supports, for example rhodium on $Al_2O_3$ (JP 59/216 852 (1984)), platinum and palladium on carbon (U.S. Pat. No. 3,520,928) or ruthenium on $Al_2O_3$, $SiO_2$ or carbon (DE 2 132 547/JP 51/68 539 (1976)) or ruthenium, chromium and manganese on $Al_2O_3$ (German Offenlegungsschrift 2 502 893/German Offenlegungsschrift 2 745 172).

Monoamino-methyl-cyclohexanes are obviously not formed at all in these reactions. In order to obtain amino-methyl-cyclohexanes in relatively large amounts, they are prepared by separate processes. Thus, for example, 1-amino-4-methyl-cyclohexane is prepared by hydrogenation of p-toluidine over a palladium (platinum)/carbon catalyst (U.S. Pat. No. 3,520,928).

A problem which is common to the processes for the ring-hydrogenation of methyl-substituted aromatic amines is the sometimes considerable formation of methyl- and amino-substituted dicyclohexyl-amines as unusable by-products. It is therefore desirable to develop a continuous fixed-bed process which can also be used on an industrial scale, by means of which both monoamino-methyl-cyclohexanes and diamino-methyl-cyclohexanes can be prepared in a desired ratio, in which losses resulting from the undesired formation of methyl- and amino-substituted dicyclohexyl-amines are avoided and in which, furthermore, as long as possible a life of the catalyst used is sought.

SUMMARY OF THE INVENTION

It has now surprisingly been found that the abovementioned requirements are met by the use of inexpensive (hydr)oxidic fixed-bed catalysts which are free of inactive support material and can therefore be worked up and disposed of in a simple manner after use.

The invention accordingly provides a continuous process for preparing a mixture of amino-methyl-cyclohexanes and diamino-methyl-cyclohexanes of the formulae

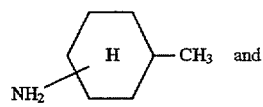

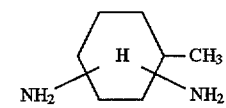

by catalytic hydrogenation of diamino-toluenes of the formula

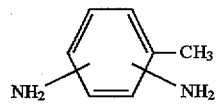

with hydrogen at reaction temperatures of from 150° to 260° C. and an $H_2$ pressure of from 20 to 500 bar, wherein the catalysts used are support-free, reduced shaped bodies comprising pressed powders of cobalt, manganese, copper and alkaline earth metal (hydr)oxides, where the shaped bodies can have a content of one or more (hydr)oxides of metals of transition group V and/or VI of the Periodic Table of the Elements (Mendeleev).

DETAILED DESCRIPTION OF THE INVENTION

In the catalysts to be used according to the invention, the proportions of Co are from 40 to 65% by weight, the proportions of Mn are from 10 to 20% by weight, the proportions of Cu are from 0.1 to 0.5% by weight, the proportions of alkaline earth metal are from 0.2 to 5% by weight and the proportions, if present, of metals of transition group V and/or VI of the Periodic Table are in total from 0.2 to 5% by weight, in each case calculated as metal. The remainder to 100% by weight is oxygen for the metals present in oxidic form.

Examples of suitable alkaline earth metals are magnesium, calcium, strontium and barium, preferably strontium and barium. Examples of suitable metals of transition group V are vanadium, niobium and tantalum, examples of suitable metals of transition group VI are chromium, molybdenum and tungsten. Like the alkaline earth metals, the metals of transition group V and/or VI can be used either individually or as a mixture of a plurality of these elements.

The support-free shaped bodies can be produced according to customary methods by pressing the metal (hydr)oxide powder mixtures (if desired after previous heating at relatively high temperatures), for example on tabletting or pelletizing machines, under high pressure. To improve the adhesion of the metal oxide particles, it is also possible to use graphite and/or adhesives in amounts of from 0.5 to 3% by weight, based on the total weight of the constituents to be pressed. Examples of shaped bodies are pellets, spheres or granules having diameters of from 3 to 7 mm. Furthermore, tabletted bodies can be provided with an axial hole to increase the external surface area. Viewed macroscopically, such shaped bodies have a smooth surface. The pressed metal oxide shaped bodies have a high compressive strength of from 300 to 800 $N/cm^2$, preferably from 400 to 600 $N/cm^2$ on the flat surface when using a flat punch or from 50 to 200 N, preferably from 80 to 140 N, on the curved surface when using a knife-like indenter. The internal surface area of the pressed metal oxide powders is from 30 to 200 $m^2/g$, preferably from 80 to 160 $m^2/g$. The compressive strength of the support-free shaped bodies can be determined in accordance with DIN 50 106, the internal surface area can be determined as described by F. M. Nelson and F. T. Eggertsen, Analyt. Chem. 30 (1958), 1387–1392 or S. J. Gregg and S. W. Sing, Adsorption, Surface Area and Porosity, London 1982, chapters 2 and 6.

The shaped bodies comprising pressed oxide powders are reduced before use. This is preferably carried out using a reducing gas comprising an inert gas/hydrogen mixture in which the hydrogen content is from 10 to 15% by volume at the beginning. The inert gas used is preferably nitrogen. The reduction is carried out, for example, over a period of about 24 hours at a reduction temperature of from 160° to 280° C. and at a pressure of from 20 to 300 bar, with the proportion of nitrogen in the gas mixture being reduced more and more in the final phase of the reduction until the gas mixture finally consists of pure hydrogen. The reduction is complete when hydrogen is no longer consumed and, as a result, water of reaction is no longer formed. The reduction preferably takes place after the shaped bodies to be reduced have been installed in the hydrogenation reactor.

Suitable starting materials for the hydrogenation according to the process of the invention are, for example: 2,4-diamino-toluene, 2,5-diamino-toluene, 2,6-diamino-toluene or mixtures of these compounds.

The process of the invention can be carried out with or without solvents. Suitable solvents which are inert under the reaction conditions are, for example, methanol, ethanol, isopropanol.

The process of the invention using the catalysts described forms mixtures of amino-methyl-cyclohexanes and diamino-methyl-cyclohexanes. Surprisingly, the ratio of the amines can be changed as a function of the hydrogenation temperature, viz. more amino-methyl-cyclohexanes are formed with increasing temperature and the opposite effect is obtained with decreasing temperature.

The process of the invention is carried out, for example, in the gas phase or a trickling phase using the catalyst arranged in a fixed bed. It is carried out using an excess of hydrogen; the amount of $H_2$ is from 10 to 120 times the amount, preferably from 10 to 80 times the amount, which is required for the hydrogenation of one benzene ring.

The process is carried out at from 150° to 260° C., preferably at from 160° to 250° C., and at a pressure of at least 20 bar, preferably at least 100 bar, particularly preferably at least 200 bar. The upper limit of the pressure employed is determined by both technical and economic considerations and is 500 bar, preferably from 200 to 400 bar.

The weight hourly space velocity over the catalyst is from 0.05 to 2 kg, preferably from 0.1 to 1 kg, particularly preferably from 0.15 to 0.6 kg, of diamino-toluenes per liter of catalyst per hour. A slight change in the proportion of amino-methyl-cyclohexanes achieved resulting from changed activity of the catalyst during the course of particularly long reaction periods can be compensated by a slight adjustment of the reaction temperature or of the other parameters. These circumstances can be monitored by analysis of the reaction mixture.

The catalyst to be used according to the invention can be installed in various apparatuses known in principle for such purposes to those skilled in the art. The process of the invention is advantageously carried out in tube reactors having one or more tubes. The reaction tubes can have lengths of, for example, from 2 to 20 m and internal diameters of from 20 to 800 mm. The catalysts have, for example, dimensions of from 2 to 10 mm and are, for example, in the form of extrudates, pellets or spheres. In the case of relatively large reactor cross sections, the catalyst bodies can also be installed on trays, in wire baskets or in similar prearranged form.

The catalysts used according to the invention have very long operating lives; up to now from 12,000 to 15,000 hours have been observed, after which the experiments were stopped without any noticeable decrease in the activity.

The reaction mixtures obtained after the hydrogenation contain virtually no methyl-substituted amino-di-N-cyclohexanes, so that particularly high contents of amino-methyl-cyclohexanes and diamino-methyl-cyclohexanes can be achieved.

The hydrogenation mixtures can be worked up by simple distillation. For such a work-up, it can be advantageous to react the respective diamino-toluenes incompletely, because the ammonia liberated in the formation of the monoamino-methyl-cyclohexanes is very readily soluble in the diamino-toluenes and can thus be removed from the off-gas from the reaction. In the distillation of the reaction products, the dissolved ammonia is distilled off first, condensed and is thus available for further use; incompletely reacted diamino-toluenes can be returned to the reaction. The unconsumed portion of the hydrogen added in excess can also be returned to the reaction; the major part of this unreacted hydrogen is advantageously recovered in a high-pressure separator so that the work of compression for the hydrogen does not have to be expended again.

The amino-methyl-cyclohexanes and diamino-methyl-cyclohexanes prepared according to the invention are, after successful separation by distillation, obtained in a purity of at least 99.9% by weight. In this purity, the specified compounds are generally usable for all further processes.

The ability of the process of the invention to be varied is shown by a strong increase in the proportion of amino-methyl-cyclohexanes compared with the diamino-methyl-cyclohexanes with rising temperature and otherwise identical conditions. Thus, for example, the proportion of amino-methyl-cyclohexanes obtained in the temperature range from about 200° to 230° C. is from 2 to 10 times that in the temperature range from 170° to 185° C.

EXAMPLES

EXAMPLE 1

An upright, heat-insulated high-pressured tube of stainless steel having an internal diameter of 30 mm and a length of 1 m, which had previously been flushed oxygen-free using nitrogen, was charged with 400 ml of a hydrogenation catalyst produced by tabletting powders of cobalt, manganese, copper, barium and molybdenum oxides. The Co content of the pellets was 53% by weight, the Mn content was 14% by weight, the Cu content was 0.18% by weight, the Ba content was 1.1% by weight and the Mo content was 1.2% by weight (remainder to 100%: oxygen). The pellets had a cylinder height of 5 mm and a diameter of 5 mm, a compressive strength of 420 $N/cm^2$ on the flat cross-sectional surface and of 125 N on the curved cylindrical surface and an internal surface area of 168 $m^2/g$. To activate the catalyst, the pellets were first dried further for 6 hours in a stream of nitrogen (temperature: max. 200°C., flow: 5 standard $m^3$ of $N_2/h$). Activation was then carried out under a nitrogen pressure of 200 bar at a temperature between 180° and 260° C., with hydrogen being gradually mixed into the nitrogen. The proportion of hydrogen mixed in was initially from 10 to 15% by volume. Over a period of 24 hours, the proportion of nitrogen was reduced more and more until finally only hydrogen flowed through the reactor. The activation was complete as soon as no more water of reaction collected in the downstream separator.

After activation of the hydrogenation catalyst, the hydrogen pressure in the reactor system was increased to 300 bar. Subsequently, 160 g/h of 2,4-diamino-toluene together with 1500 standard l/h of hydrogen under a pressure of 300 bar were pumped through the high-pressure tube from the top downward as a trickling phase. The 2,4-diamino-toluene was heated to a temperature of 180° C. in an upstream, electrically heated heat exchanger before entering the reactor. The reaction product leaving the reaction tube was cooled to a temperature of ≦60° C. under 300 bar of hydrogen pressure in a second heat exchanger (water cooler) and separated in a gas separator from excess hydrogen which could be returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (figures in % by area; the remainder to 100% is by-products):

| Running time (h) | Temperature (°C.) | 2- and 4-Amino-methyl-cyclohexane (% by area) | 2,4-Diamino-methyl-cyclohexane (% by area) | 2,4-Diamino-toluene (% by area) |
| --- | --- | --- | --- | --- |
| 254 | 250 | 36.8 | 53.9 | 2.0 |
| 278 | 245 | 26.0 | 63.0 | 6.6 |
| 302 | 240 | 25.2 | 48.9 | 22.2 |
| 326 | 235 | 23.2 | 37.2 | 34.6 |
| 350 | 220 | 18.8 | 28.8 | 35.1 |
| 422 | 210 | 15.5 | 24.1 | 58.0 |
| 494 | 200 | 8.3 | 15.0 | 75.8 |
| 518 | 180 | 3.9 | 9.1 | 86.5 |

EXAMPLE 2

An upright, heat-insulated high-pressure tube of stainless steel having an internal diameter of 45 mm and a length of 1 m, which had previously been flushed oxygen-free using nitrogen, was charged with 1400 ml of a hydrogenation catalyst produced by tabletting powders of cobalt, manganese, copper, barium and molybdenum oxides. The Co content of the pellets was 53% by weight, the Mn content was 14% by weight, the Cu content was 0.2% by weight, the Ba content was 0.9% by weight and the Mo content was 1.1% by weight. The pellets had a cylinder height of 5 mm and a diameter of 5 mm, a compressive strength of 425 N/cm² on the cross-sectional surface and of 160 N on the cylindrical surface and an internal surface area of 180 m²/g.

After activation of the hydrogenation catalyst as in Example 1, the hydrogen pressure in the reactor system was increased to 300 bar. Subsequently, 240 g/h of a mixture of 80% by weight of 2,4-diamino-toluene and 20% by weight of 2,6-diamino-toluene together with 5000 standard l/h of hydrogen under a pressure of 300 bar were pumped through the high-pressure tube from the top downward as a trickling phase. The diamino-toluene mixture was heated to a temperature of 180° C. in an upstream electrically heated heat exchanger before entering the reactor. The reaction product leaving the reaction tube was cooled to a temperature of <60° C. under 300 bar of hydrogen pressure in a second heat exchanger (water cooler) and separated in a gas separator from excess hydrogen which could be returned to the hydrogenation system. After further cooling to a temperature of <30° C. and depressurization to atmospheric pressure, the reaction product was analyzed by gas chromatography. Under steady-state reaction conditions, the following production composition was obtained as a function of the reaction temperatures (figures in % by area; the remainder to 100% is by-products):

| Running time (h) | Temperature (°C.) | 2- and 4-Amino-methyl-cyclohexane (% by area) | 2,4- and 2,6-Diamino-methyl-cyclohexane (% by area) | 2,4- and 2,6-Diamino-toluene (% by area) |
| --- | --- | --- | --- | --- |
| 54 | 180 | 4.8 | 25.9 | 66.8 |
| 102 | 200 | 5.3 | 36.5 | 58.7 |
| 324 | 210 | 10.3 | 65.4 | 20.3 |
| 396 | 215 | 22.2 | 59.2 | 18.6 |
| 588 | 230 | 38.0 | 50.5 | 6.1 |

EXAMPLE 3

An upright, heat-insulated high-pressure tube of stainless steel having an internal diameter of 30 mm and a length of 1 m, which had previously been flushed oxygen-free using nitrogen, was charged with 400 ml of a hydrogenation catalyst produced by tabletting powders of cobalt, manganese, copper, barium and vanadium oxides. The Co content of the pellets was 52% by weight, the Mn content was 16% by weight, the Cu content was 0.18% by weight, the Ba content was 0.91% by weight and the V content was 1.1% by weight (remainder to 100% by weight: oxygen). The pellets had a cylinder height of 5 mm and a diameter of 5 mm, a compressive strength of 420 N/cm² on the cross-sectional surface and of 160 N on the cylindrical surface and an internal surface area of 180 m²/g.

The pellets were first dried for 6 hours in a stream of nitrogen (temperature: max. 200° C., flow: 5 standard m³ of $N_2$/h). Activation was carried out under a nitrogen pressure of 200 bar at a temperature between 180° and 280° C., with hydrogen gradually being mixed into the nitrogen. The initial proportion of hydrogen mixed in was from 10 to 15% by volume. Over a period of 24 hours, the proportion of nitrogen was reduced more and more until finally only hydrogen flowed through the reactor. The activation was complete as soon as no more water of reaction collected in the downstream separator.

After activation of the hydrogenation catalyst, the hydrogen pressure in the reactor system was increased to 280 bar. Subsequently, 100 g/h of a mixture of 80% by weight of 2,4-diamino-toluene and 20% by weight of 2,6-diamino-toluene together with 1500 standard l/h of hydrogen under a pressure of 280 bar were pumped through the high-pressure tube from the top downward as a trickling-phase. The diamino-toluene mixture was heated to a temperature of 160° C. in an upstream electrically heated heat exchanger before entering the reactor. The reaction product leaving the reaction tube was cooled to a temperature of <60° C. under 300 bar of hydrogen pressure in a second heat exchanger (water cooler) and separated in a gas separator from excess hydrogen which could be returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (figures in % by area; the remainder to 100% is by-products):

| Running time (h) | Temperature (°C.) | 2- and 4- Amino-methyl-cyclohexane (% by area) | 2,4- and 2,6- Diamino-methyl-cyclohexane (% by area) | 2,4- and 2,6- Diamino-toluene (% by area) |
|---|---|---|---|---|
| 80  | 180 | 4.6  | 43.8 | 49.5 |
| 124 | 200 | 6.8  | 46.2 | 43.9 |
| 198 | 210 | 12.4 | 51.5 | 33.8 |
| 240 | 215 | 24.8 | 59.1 | 15.2 |
| 588 | 230 | 31.7 | 61.2 | 5.4  |

EXAMPLE 4

An upright, heat-insulated high-pressure tube of stainless steel having an internal diameter of 30 mm and a length of 1 m, which had previously been flushed oxygen-free using nitrogen, was charged with 400 ml of a hydrogenation catalyst produced by tabletting powders of cobalt, manganese, copper and barium oxides. The Co content of the pellets was 54% by weight, the Mn content was 14.5% by weight, the Cu content was 0.18% by weight and the Ba content was 1.05% by weight. The pellets had a cylinder height of 5 mm and a diameter of 5 mm, a compressive strength of 438 N/cm$^2$ on the flat cylinder surface and of 115 N on the curved surface and an internal surface area of 178 m$^2$/g.

The pellets were, as described in Example 1, dried and activated. After activation, the hydrogen pressure in the reactor system was increased to 280 bar. Subsequently, 100 g/h of a mixture of 80% by weight of 2,4-diamino-toluene and 20% by weight of 2,6-diamino-toluene together with 1.5 standard m$^3$/h of hydrogen under a pressure of 280 bar were pumped through the high-pressure tube as a trickling phase. The diamino-toluene mixture to be hydrogenated was heated to a temperature of 175° C. in an upstream electrically heated heat exchanger before entering the high-pressure tube. The reaction product leaving the reaction tube was, as described in Example 1, cooled and separated from excess hydrogen. After further cooling to a temperature of <30° C. and depressurization to atmospheric pressure, the reaction product was analyzed by gas chromatography. Under steady-state reaction conditions, the following product composition was obtained as a function of the reaction temperatures (the remainder to 100% is by-products):

| Running time (h) | Temperature (°C.) | 2- and 4- Amino-methyl-cyclohexane (% by area) | 2,4- and 2,6- Diamino-methyl-cyclohexane (% by area) | 2,4- and 2,6- Diamino-toluene (% by area) |
|---|---|---|---|---|
| 286 | 180 | 2.1  | 28.6 | 65.1 |
| 348 | 200 | 6.2  | 38.4 | 51.6 |
| 412 | 210 | 11.0 | 45.2 | 46.2 |
| 486 | 220 | 15.4 | 52.2 | 32.0 |
| 526 | 230 | 22.8 | 48.7 | 26.6 |
| 612 | 240 | 28.1 | 64.8 | 4.2  |
| 718 | 250 | 32.0 | 65.3 | 0.9  |

What is claimed is:

1. A continuous process for preparing a mixture of an amino-methyl-cyclohexane and a diamino-methyl-cyclohexane of the formulae

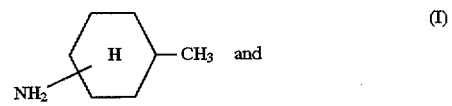

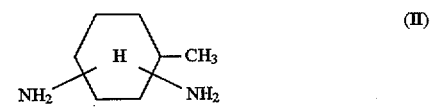

by catalytic hydrogenation of a diamino-toluene of the formula

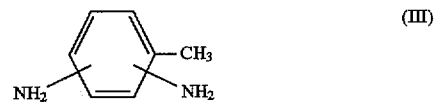

with hydrogen at a reaction temperature of from 150° to 260° C. and an H$_2$ pressure of from 20 to 500 bar, wherein the catalysts used are support-free, reduced shaped bodies comprising pressed powders of cobalt, manganese, copper and alkaline earth metal (hydr)oxides, where the shaped bodies can have a content of one or more (hydr)oxides of metals of transition group V and/or VI of the Periodic Table of the Elements (Mendeleev).

2. The process of claim 1, wherein the shaped bodies comprising pressed metal oxides comprise, before reduction, from 40 to 65% by weight of cobalt, from 10 to 20% by weight of manganese, from 0.1 to 0.5% by weight of copper, from 0.2 to 5% by weight of alkaline earth metal and, if desired, from 0.2 to 5% by weight of elements of transition group V and/or VI of the Periodic Table, in each case calculated as metal, where the percentages are based on the total mount of metal oxide powder mixture and the remainder to 100% by weight is oxygen.

3. The process of claim 1, wherein the shaped bodies have a compressive strength of from 20 to 800 N/cm$^2$ on flat surfaces, a compressive strength of from 50 to 200 N on curved surfaces and an internal surface area of from 30 to 200 m$^2$/g.

4. The process of claim 3, wherein the shaped bodies have a compressive strength of from 250 to 600 N/cm$^2$ on flat surfaces.

5. The process of claim 3, wherein the shaped bodies have a compressive strength of from 80 to 140 N on curved surfaces.

6. The process of claim 3, wherein the shaped bodies have an internal surface area of from 80 to 160 m$^2$/g.

7. The process of claim 1, carried out at an H$_2$ pressure of from 20 to 400 bar.

8. The process of claim 7, carried out at an H$_2$ pressure of from 100 to 400 bar.

9. The process of claim 8, carried out at an H$_2$ pressure of from 200 to 400 bar.

10. The process of claim 1, carried out at a temperature of from 160° to 250° C.

11. The process of claim 1, carried out continuously in the gas phase or a trickling phase over fixed-bed catalysts at a weight hourly space velocity over the catalyst of from 0.05 to 2 kg of diamino-toluenes per liter of catalyst per hour.

12. The process of claim 11, carried out at a weight hourly space velocity of from 0.1 to 1 kg of diamino-toluenes per liter of catalyst per hour.

13. The process of claim 12, carried out at a weight hourly space velocity of from 0.15 to 0.6 kg of diamino-toluenes per liter of catalyst per hour.

14. The process of claim 1, wherein the shaped bodies are reduced by treatment with hydrogen at a temperature of from 160° to 280° C. and at from 20 to 300 bar before use, preferably after installation in the hydrogenation reactor, where the hydrogen is used as an $H_2$/inert gas mixture at the beginning of the reduction and the proportion of inert gas is removed completely during the course of the reduction.

* * * * *